(12) United States Patent
Nowak

(10) Patent No.: US 10,154,887 B2
(45) Date of Patent: Dec. 18, 2018

(54) SUPPORT DEVICE FOR A DRAIN SYSTEM USED IN POST-SURGICAL PROCEDURES

(71) Applicant: Post-Op Provisions, LLC, Eden Prairie, MN (US)

(72) Inventor: Deborah M. Nowak, Eden Prairie, MN (US)

(73) Assignee: Post-Op Provisions, LLC, Eden Prairie, MN (US)

( * ) Notice: Subject to any disclaimer, the term of this patent is extended or adjusted under 35 U.S.C. 154(b) by 295 days.

(21) Appl. No.: 15/281,622

(22) Filed: Sep. 30, 2016

(65) Prior Publication Data

US 2017/0095648 A1    Apr. 6, 2017

Related U.S. Application Data

(60) Provisional application No. 62/236,370, filed on Oct. 2, 2015.

(51) Int. Cl.
*A61M 27/00* (2006.01)
*A61B 50/20* (2016.01)
*A61M 1/00* (2006.01)

(52) U.S. Cl.
CPC .......... *A61B 50/20* (2016.02); *A61M 1/0003* (2013.01); *A61M 1/0011* (2013.01); *A61M 2209/088* (2013.01)

(58) Field of Classification Search
CPC ... A61B 50/20; A61M 1/0003; A61M 1/0011; A61M 2209/088
See application file for complete search history.

(56) References Cited

U.S. PATENT DOCUMENTS

| 2,943,775 A | * | 7/1960 | Mack | ....................... A62B 9/04 224/628 |
| 5,716,334 A | | 2/1998 | Wade | |
| 5,980,499 A | | 11/1999 | Ekey | |

(Continued)

OTHER PUBLICATIONS

Baumgartens Detachable Breakaway Lanyard, available for sale by Wal-Mart. http://www.walmart.com/ip/Baumgartens-Detachable-Breakaway-Lanyards-X-36-Length-Black-Nylon-Plastic-Metal-BAU65564/41083822.

*Primary Examiner* — Tatyana Zalukaeva
*Assistant Examiner* — Kai Weng
(74) *Attorney, Agent, or Firm* — Patterson Thuente Pedersen, P.A.

(57) ABSTRACT

A support device configured to support post-surgical drain bulbs at locations adjacent to a body of a wearer. The support device including a band of flexible material having a first end and a second end defining a band length there between, the band further including a pair of D-rings positioned proximate to the first end of the band and sized to accommodate a portion of the band proximate to the second end of the band, one or more snap fastener parts positioned proximate to the second end of the band and configured to selectively couple to one or more snap fastener counterparts positioned along the band length between the first end and the second end, and a band of hook and loop fastener material fixedly coupled to an outer surface of the band along the length of the band from a point proximate to the first end to a point proximate to the second end and configured to selectively couple to one or more securement members comprised of a counterpart to the hook and loop fastener material.

8 Claims, 6 Drawing Sheets

(56) References Cited

U.S. PATENT DOCUMENTS

| | | | |
|---|---|---|---|
| D544,095 S | 6/2007 | McLaughlin | |
| 7,927,311 B1 | 4/2011 | Bachelder | |
| 2005/0251895 A1* | 11/2005 | Farrah ..................... | A41D 1/08 2/227 |
| 2006/0173427 A1 | 8/2006 | Urbina et al. | |
| 2008/0108948 A1 | 5/2008 | Beaver | |
| 2008/0294128 A1 | 11/2008 | Richards | |
| 2011/0230863 A1 | 9/2011 | Lentini | |
| 2014/0312091 A1 | 10/2014 | Anderson | |

\* cited by examiner

SUPPORT DEVICE FOR A DRAIN SYSTEM USED IN POST-SURGICAL PROCEDURES

RELATED APPLICATION INFORMATION

The present application claims the benefit of U.S. Provisional Application No. 62/236,370 filed Oct. 2, 2015, which is hereby incorporated herein in its entirety by reference.

TECHNICAL FIELD

The present disclosure relates generally to surgical drainage support devices. More particularly, the present disclosure relates to washable bands of flexible material configured to be worn around a wearer for the support of one or more post-surgical drain bulbs.

BACKGROUND

Following certain types of surgery, especially surgery involving the removal of tissue, the resulting body cavity may fill with fluid. Examples of such surgery include mastectomies and lumpectomies. To relieve swelling and infection that may occur if the fluid is left in the body, one end of a drainage tube, which may be two feet long or longer, is inserted through a surgical incision into the cavity and is normally sutured, or stitched directly to the skin at the surgery site, and the other end of the drainage tube is attached to a post-surgical fluid drainage bulb or plastic bottle receptacle for collecting the fluid. Such drainage bulbs, also known as bulb drains or suction reservoirs, sometimes marketed under the names JACKSON-PRATT, HEMOVAC and DAVOL, are capable of creating a negative pressure in the body cavity to facilitate drainage and hold the skin against the muscle until it heals.

Some postoperative procedures require multiple tubes and drainage bulbs. Depending on the surgery and the amount of fluid buildup expected. The number of drainage tubes and receptacles utilized can vary. When many drainage tubes are utilized, the managing of the tubes and their associated receptacles pose certain problems. In the past, it was common to pin the receptacles to the clothing or gown worn by the patient or to the bandage for the incision itself. While not very comfortable, this procedure is somewhat effective in the hospital where an open gown is worn, thereby easing the ability of the patient to accommodate basic bodily functions. Furthermore, the awkwardness and discomfort is increased with multiple sets of bottles and tubes. In addition, outside of the hospital, where patients wear standard, relatively constricting clothes, it is not practicable to use such means to support drain bulbs. With the advent of insurance company mandates on shorter hospital stays for many types of surgeries, the problems associated with supporting drain bulbs have become more prevalent.

It is not uncommon for a postoperative patient to be discharged from the hospital or clinic with four or more suction reservoir bulbs pinned to their clothing or post surgical dressings. For example, the plastic tabs or loops of the drain bulbs may be pinned directly to a wide elastic band wrapped around the patient's chest. In order to shower, this patient must first unpin the bulbs and then remove the elastic band. At this point there is nothing to attach the bulbs to, and the pa ent or an assistant may be required to hold the bulbs and tubes in their hands while the patient attempts to shower, which is extremely cumbersome and runs the risk of dropping the bulbs.

Others have attempted to overcome these problems by providing belts or harnesses that encircle the chest area or the waist of a postoperative patient to support fluid drainage receptacles. While these devices may resolve some of the problems associated with supporting post operative drainage receptacle, they are not particularly comfortable after being worn for extended periods of time, can irritate the skin, and due to their structure cannot effectively support a plurality of drainage bulbs at locations adjacent to the body of the wearer to allow easy access and avoid tangling of the drainage tubes.

Accordingly, what is needed in the industry is a lightweight, comfortable support system that is highly customizable to the patient that can be worn in a variety of ways and configurations.

SUMMARY

Embodiments of the present disclosure meet the need of the industry for a lightweight, comfortable support system configured to support one or more post-surgical drain bulbs at locations adjacent to a body of a wearer to allow easy access and avoid tangling and stress on drain tubes in the form of a highly customizable belt or lanyard that can be worn in a variety of ways and configurations.

One embodiment of the present disclosure provides support system including a washable band of flexible material configured to be worn around a waist of the wearer. In one embodiment, the band has a first end and a second end defining a band length there between, wherein the band length has an outer surface and an inner surface. In one embodiment, the band further includes a pair of D-rings positioned proximate to the first end of the band and sized to accommodate a portion of the band proximate to the second end of the band. In one embodiment, the band further includes one or more snap fastener parts positioned proximate to the second end of the band and configured to selectively couple to one or more snap fastener counterparts positioned along the band length between the first end and the second end. In one embodiment, the band further includes a band of hook and loop fastener material fixedly coupled to the outer surface of the band along the length of the band from a point proximate to the first end to a point proximate to the second end and configured to selectively couple one or more securement members comprised of a counterpart to the hook and loop fastener material fixedly coupled to the outer surface of the band.

In some embodiments, the system further includes one or more post-surgical drain bulbs, wherein each surgical drain bulb has a loop though which at least one of the one or more securement members passes to secure the post-surgical drain bulb to the band. In other embodiments, the post-surgical drain bulbs are provided separately.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which.

Figure 1:
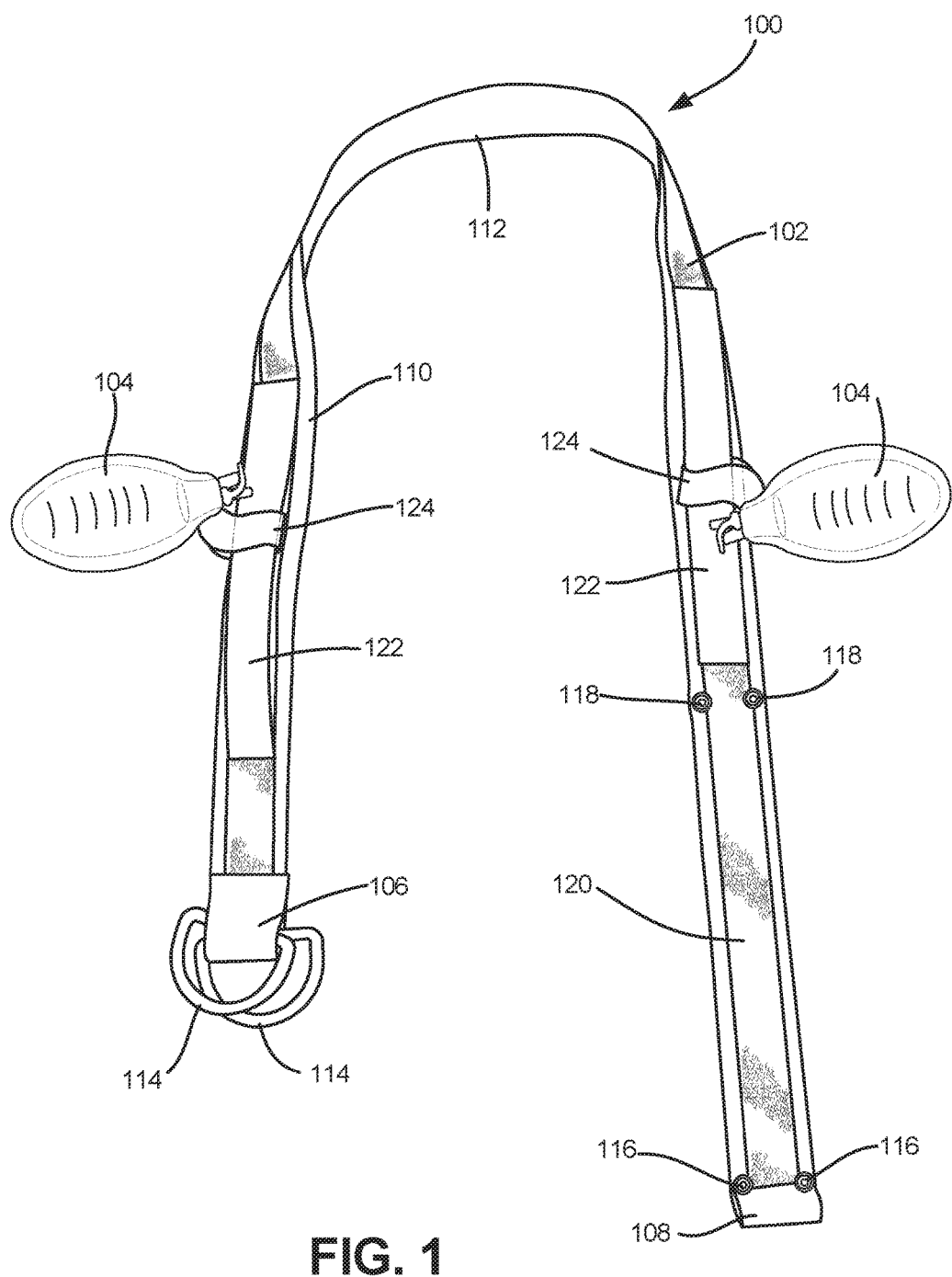
FIG. 1 depicts a post-surgical drain bulb support system in accordance with an embodiment of the disclosure.

While embodiments of the disclosure are amenable to various modifications and alternative forms, specifics thereof are shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure as defined by the appended claims.

DETAILED DESCRIPTION OF THE DRAWINGS

Referring to FIG. 1, a support system 100 according to a disclosed embodiment is depicted. Support system 100 generally includes a band of material 102 and one or more post-surgical drain bulbs 104.

In one embodiment, band of material 102 has a first end 106 and a second end 108 defining a band length there between. The band length can have an outer surface 110 and an inner surface 112. In one embodiment, band of material 102 can be constructed of fabric stock, such as a seamless woven tube fabric stock. In other embodiments, the band of material 102 can be constructed of other materials.

In one embodiment, band of material 102 is washable. In one embodiment, band of material 102 is flexible. Band of material 102 can be highly customizable, and can be configured to be worn around the waist of a wearer, across the chest of the wearer, slung around the neck, slung around an arm of a wearer, or attached to other extremities of the wearer.

In one embodiment, band of material 102 further includes one or more D-rings 114. In some embodiments, D-rings 114 are positioned proximate to the first end 106 of the band 102. The D-rings 114 can be sized to accommodate a portion of the band 102 proximate to the second end 108. In one embodiment, D-rings 114 are constructed of plastic. In other embodiments, b-rings 114 are constructed of metal, or some other material.

In one embodiment, band of material 102 further includes at least one snap fastener part 116 positioned proximate to the second end 108 of the band 102. In one embodiment, the at least one snap fastener part 116 is configured to selectively couple to at least one snap fastener counterpart 118 positioned along the band length between the first end 106 and the second end 108.

In one embodiment, band of material 102 further includes a band of hook and loop fastener material 120 fixedly coupled to the outer surface 110 of the band 102. In one embodiment, the band of hook and loop fastener material 120 is fixedly coupled along the length of the band 102 from a point proximate to the first end 106 to a point proximate to the second end 108. In one embodiment, the band of hook and loop fastener material 120 is configured to selectively couple at least one securement member 122 comprised of a counterpart to the hook and loop fastener material 120 to the outer surface of the band.

Figure 2:
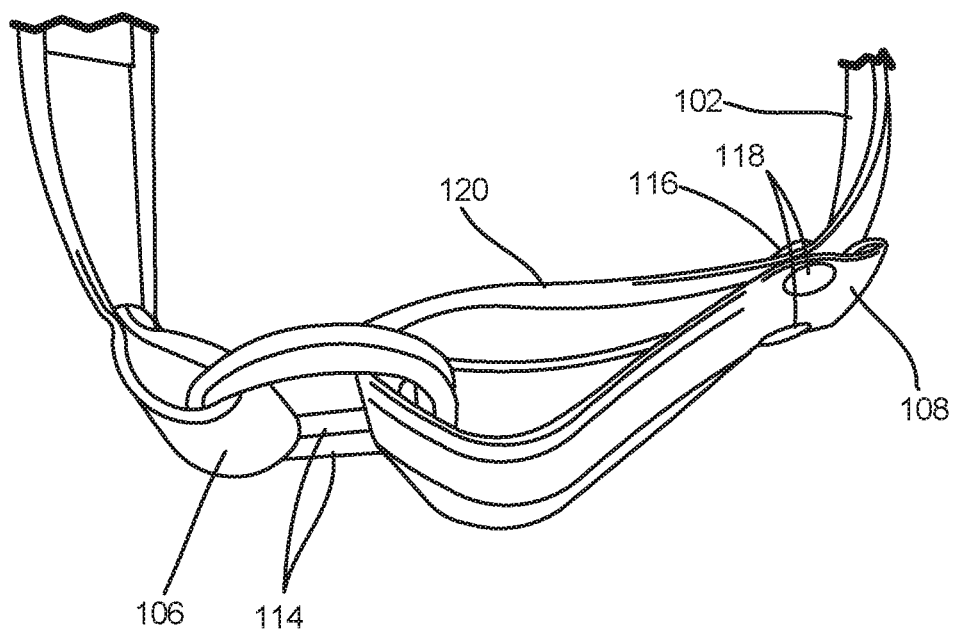
FIG. 2 depicts a band of material secured to itself, thereby forming a loop, in accordance with an embodiment of the disclosure.

Referring to FIG. 2, a portion of the band 102 proximate to the second end 108 has been fed through a pair of D-rings 114 positioned proximate to the first end 106 of the band 102 and secured to a portion of the band length between the first end 106 and the second end 108 via a pair of snap fasteners 116, 118, as well as a portion of the band of hook and loop fastener material 120.

Figure 3:
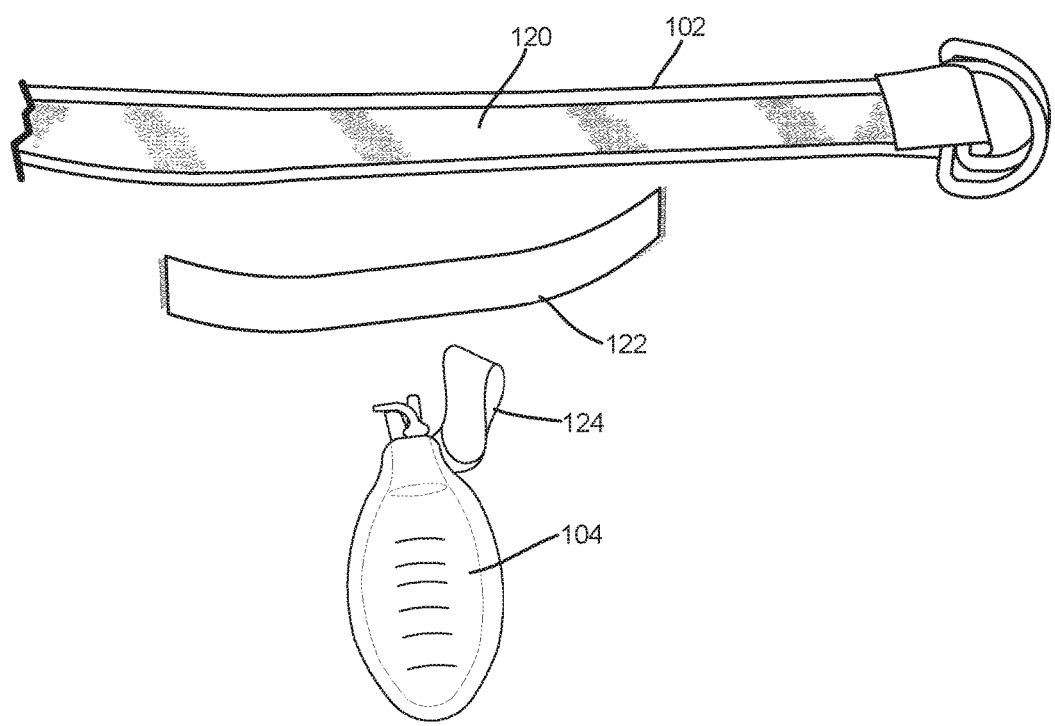
FIG. 3 depicts a post-surgical drain bulb, a band of material and a securement member in accordance with an embodiment of the disclosure.
Figure 4:
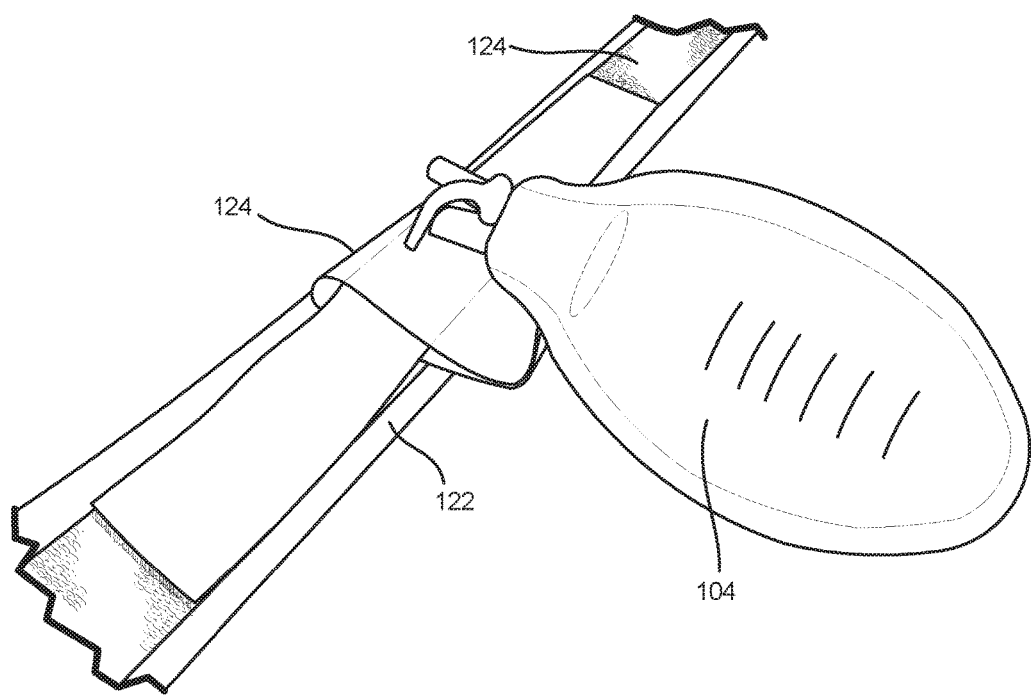
FIG. 4 depicts a post-surgical drain bulb secured to a band of material via a securement member in accordance with an embodiment of the disclosure.

The support system 100 can include at least one post-surgical drain bulb 104 having a loop 124 though which at least one of the one or more securement members 122 can pass to secure the post-surgical drain bulb 104 to the band 102. FIG. 3 depicts a band securement member 122 separate from a band of material 102. FIG. 4 depicts a post-surgical drain bulb 104 secured to a band of material 102 via a securement member 122. In other embodiments, the post-surgical drain bulbs 104 are provided separately, and are not considered part of the support system 100.

In operation, the support system 100 can be provided to the wearer. In one method of use, one or more post-surgical drain bulbs 104, which in some embodiments are provided separately from the support system 100, can be secured to the band 102 by passing at least one of the one or more securement members 122 through a loop 124 on each post-surgical drain 104 and coupling the at least one securement member 124 to the band of hook and loop fastener material 120 fixedly coupled to the outer surface 110 of the band 102.

Figure 5:
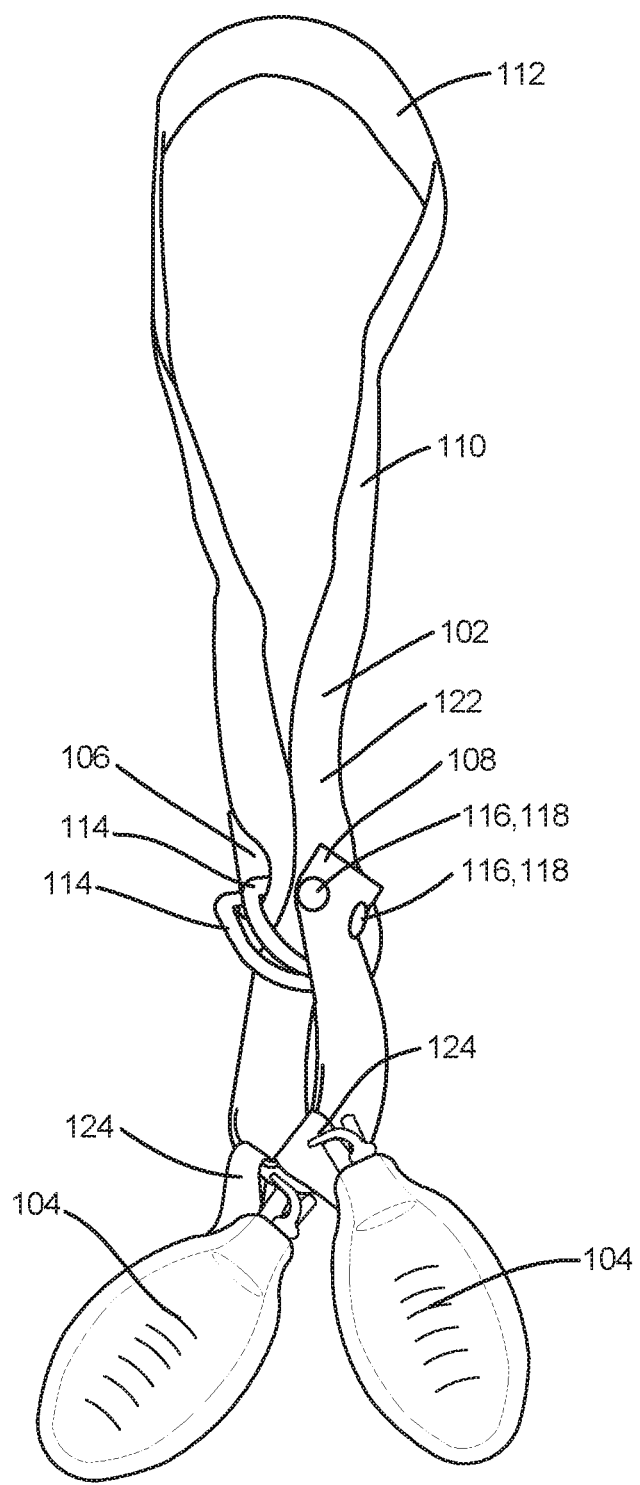
FIG. 5 depicts a post-surgical drain bulb secured to a band of material in accordance with in another method of use of the disclosure.

Referring to FIG. 5, in another method of use, a portion of the band proximate to the second end 108 of the band can be passed through loops 124 of one or more post-surgical drain bulbs 104, thereby securing the one or more post-surgical drain bulbs 104 to the band 102. In this embodiment, the second end 108 of the band can further be passed at least one of the pair of b-rings 114 positioned proximate to the first end 106 of the band and securing the second end 108 of the band to a portion of the band length between the first end and the second end via at least one of the one or more snap fasteners 116, 118, the band of hook and loop fastener material 122, or a combination thereof. In further methods of use, one or more of the above described methods of use can be combined.

In one method of use, the wearer, or a practitioner assisting the wearer, can fasten the band 102 around the waist of the wearer by passing a portion of the band proximate to the second end 108 of the band through at least one of the pair of D-rings 114 positioned proximate to the first end 106 of the band and securing the second end 108 of the band to a portion of the band length between the first end and the second end via at least one of the one or more snap fasteners 116, 118, the band of hook and loop fastener material 122, or a combination thereof.

In another method of use, the wearer, or a practitioner assisting the wearer, can form band 102 into a loop, or a series of loops via D-rings 114, fasteners 116, 118, hook and loop fastener material 122, or a combination thereof, and sling the band 102 around the neck of the wearer, across the chest of the wearer, around an arm of a wearer, or around other extremities of the wearer. For example, in one method of use, a portion of the band proximate to the second end 108 of the band can be passed through at least one of the pair of D-rings 114 positioned proximate to the first end 106 of the band and secured to a portion of the band length between the first end and the second end via at least one of the one or more snap fasteners 116, 118, the band of hook and loop fastener material 122, or a combination thereof.

Figure 6:
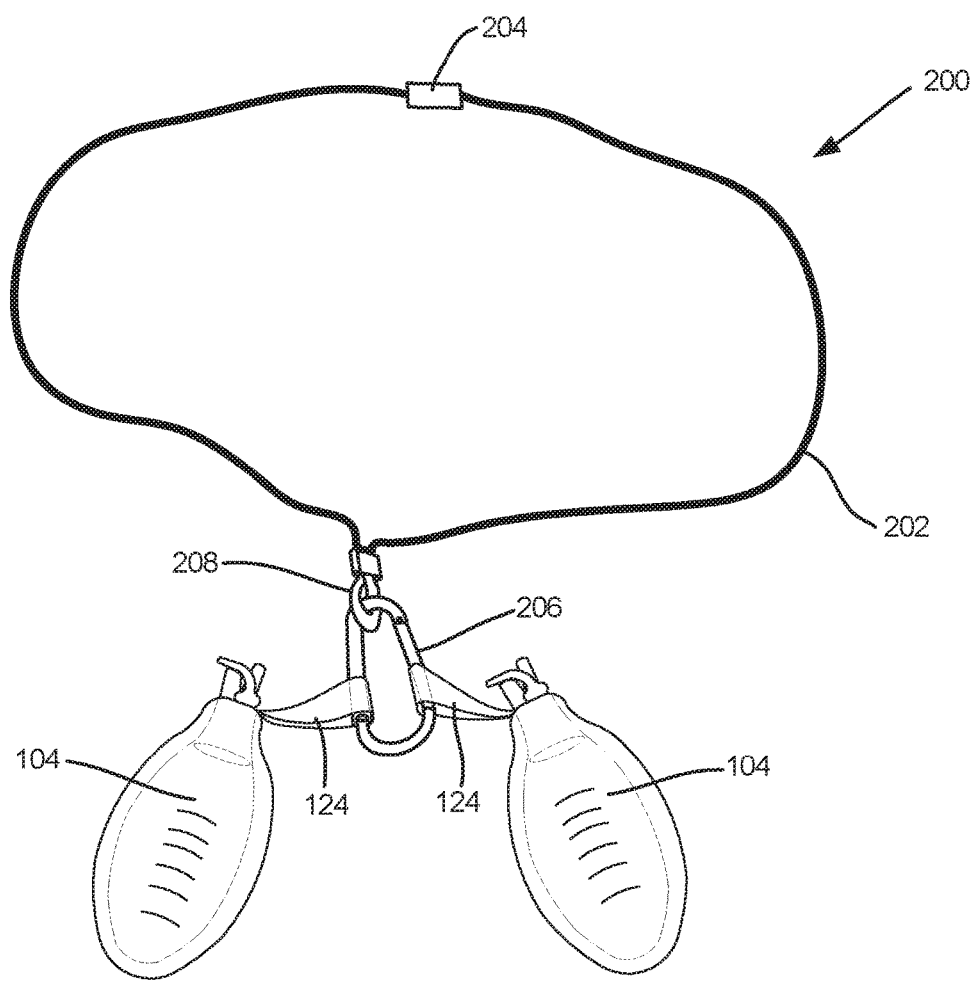
FIG. 6 depicts a post-surgical drain bulb support system in accordance with another embodiment of the disclosure.

Referring to FIG. 6, a support system 200 according to another disclosed embodiment is depicted. Support system 200 generally includes a lanyard 202, a quick release mechanism 204 and a clip 206 configured to be selectively coupled to the loop 124 of at least one post-surgical drain bulb 104. In some embodiments, lanyard 202 can be a nylon cord, or court constructed of other material. In one embodiment, lanyard 202 can include a loop 208 to which clip 206 is operably coupled. In other embodiments, the clip 206 connects directly to lanyard 202 without any loops defined therein.

In one embodiment, quick release mechanism 204 can include a break-away safety clip having a first portion and a second portion that when coupled together are configured to separate from one another when tension exceeding a given threshold is applied to the first and second portions. In this manner, the quick release mechanism 204 may promote safety by enabling the lanyard 202 to break away from a user's neck if the tension threshold is exceeded.

Clip 206 can be configured to couple one or more post-surgical drain bulb 104 to the lanyard. In one embodiment, clip 206 can include a hinged clip member, such as a carabineer. In one embodiment, clip 206 can lock to inhibit inadvertent release of the one or more post-surgical drain bulb 104.

Persons of ordinary skill in the relevant arts will recognize that embodiments may comprise fewer features than illustrated in any individual embodiment described above. The embodiments described herein are not meant to be an exhaustive presentation of the ways in which the various features may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

What is claimed is:

1. A lightweight, comfortable support system configured to support one or more post-surgical drain bulbs at locations adjacent to a body of a wearer to allow easy access and avoid tangling and stress on drain tubes, the support system comprising:
    a washable band of flexible material configured to be worn around a waist of the wearer, the band having a first end and a second end defining a band length there between, the band length having an outer surface and an inner surface, the band further including:
        a pair of D-rings positioned proximate to the first end of the band and sized to accommodate a portion of the band proximate to the second end of the band;
        one or more snap fastener parts positioned proximate to the second end of the band and configured to selectively couple to one or more snap fastener counterparts positioned along the band length between the first end and the second end; and
        a band of hook and loop fastener material fixedly coupled to the outer surface of the band along the length of the band from a point proximate to the first end to a point proximate to the second end and configured to selectively couple one or more securement members, comprised of a counterpart to the hook and loop fastener material, to the outer surface of the band; and
    one or more post-surgical drain bulbs, each surgical drain bulb having a loop though which at least one of the one or more securement members passes to secure the post-surgical drain bulb to the band.

2. The support system of claim 1, wherein the pair of D-rings are constructed of plastic.

3. The support system of claim 1, wherein the pair of D-rings are stitched to the washable band of flexible material.

4. The support system of claim 1, wherein the support system is configured to at least one of be worn around the waist of a wearer, be worn across the chest of the wearer, be slung around the neck, be slung around an arm of a wearer, and be attached to other extremities of the wearer.

5. A method of using lightweight, comfortable support device configured to support one or more post-surgical drain bulbs at locations adjacent to a body of a wearer to allow easy access and avoid tangling and stress on drain tubes, the method comprising:
    providing a washable band of flexible material configured to be worn around a waist of the wearer, the band having a first end and a second end defining a band length there between, the band length having an outer surface and an inner surface, the band further including a pair of D-rings positioned proximate to the first end of the band and sized to accommodate a portion of the band proximate to the second end of the band, one or more snap fastener parts positioned proximate to the second end of the band and configured to selectively couple to one or more snap fastener counterparts positioned along the band length between the first end and the second end, and a band of hook and loop fastener material fixedly coupled to the outer surface of the band along the length of the band from a point proximate to the first end to a point proximate to the second end and configured to selectively couple one or more securement members, comprised of a counterpart to the hook and loop fastener material, to the outer surface of the band;
    fastening the band around the waist of the wearer by passing a portion of the band proximate to the second end of the band through at least one of the pair of D-rings positioned proximate to the first end of the band and securing the second end of the band to a portion of the band length between the first end and the second end via at least one of the one or more snap fasteners, the band of hook and loop fastener material, or a combination thereof;

securing one or more post-surgical drain bulbs to the band by passing at least one of the one or more securement members through a loop on each post-surgical drain and coupling the at least one securement member to the band of hook and loop fastener material fixedly coupled to the outer surface of the band.

6. The method of claim 5, wherein the pair of D-rings are constructed of plastic.

7. The method of claim 5, wherein the pair of D-rings are stitched to the washable band of flexible material.

8. The method of claim 5, wherein the support system is configured to at least one of be worn around the waist of a wearer, be worn across the chest of the wearer, be slung around the neck, be slung around an arm of a wearer, and be attached to other extremities of the wearer.

\* \* \* \* \*